(12) United States Patent
Shahinpoor et al.

(10) Patent No.: US 7,060,094 B2
(45) Date of Patent: Jun. 13, 2006

(54) ACCOMMODATING ZONULAR MINI-BRIDGE IMPLANTS

(75) Inventors: Mohsen Shahinpoor, Albuquerque, NM (US); David Soltanpour, Larchmont, NY (US)

(73) Assignee: Ophthalmotronics, Inc., Albuquerque, NM (US)

( * ) Notice: Subject to any disclaimer, the term of this patent is extended or adjusted under 35 U.S.C. 154(b) by 486 days.

(21) Appl. No.: 09/759,766

(22) Filed: Jan. 12, 2001

(65) Prior Publication Data

US 2003/0028248 A1    Feb. 6, 2003

Related U.S. Application Data

(60) Provisional application No. 60/223,141, filed on Aug. 7, 2000.

(51) Int. Cl.
*A61F 2/14* (2006.01)
(52) U.S. Cl. .................. 623/4.1; 623/6.43; 623/14.13
(58) Field of Classification Search ................ 623/4.1, 623/6.37, 6.38, 6.43, 11.11, 14.13, 905
See application file for complete search history.

(56) References Cited

U.S. PATENT DOCUMENTS

| | | | |
|---|---|---|---|
| 4,253,199 A | 3/1981 | Banko | |
| 4,254,509 A | 3/1981 | Tennant | |
| 4,409,691 A | 10/1983 | Levy | |
| 4,765,329 A | 8/1988 | Cumming et al. | |
| 4,786,445 A | 11/1988 | Portnoy et al. | |
| 4,790,847 A | 12/1988 | Woods | |
| 4,842,601 A | 6/1989 | Smith | |
| 4,888,012 A | 12/1989 | Horn et al. | |
| 4,888,016 A * | 12/1989 | Langerman | 623/6.39 |
| 4,892,543 A | 1/1990 | Turley | |
| 4,961,744 A | 10/1990 | Kilmer et al. | |
| 4,994,082 A | 2/1991 | Richards et al. | |
| 5,108,429 A | 4/1992 | Wiley | |
| 5,147,284 A | 9/1992 | Fedorov et al. | |
| 5,152,789 A | 10/1992 | Willis | |
| 5,250,167 A | 10/1993 | Adolf | |

(Continued)

FOREIGN PATENT DOCUMENTS

CA    2 358 485 A1 *   7/2000

(Continued)

OTHER PUBLICATIONS von Hemholtz (von Hemholtz H., "Uber die akkommodation des auges", Albrecht von Graefef Arch Ophthalmol, 1855; 1:1089).

(Continued)

*Primary Examiner*—David H. Willse
*Assistant Examiner*—Javier G. Blanco
(74) *Attorney, Agent, or Firm*—Dennis F. Armijo

(57) ABSTRACT

Surgical correction of presbyopia and hyperopia by a circularly distributed assembly of mini-bridges implanted between the interior surfaces of the ciliary muscle and the exterior surface of the lens capsule, for augmenting the transmission of the contraction force of the ciliary muscle/zonule assembly to the lens capsule. The lens is symmetrically squeezed by mini-bridges acting in concert with the ciliary muscle thus changing the curvature of the lens. The mini-bridges are composite synthetic muscles comprising either passive biocompatible mini-bridges made with polymeric gels, silicone polymers or a composite, electromagnetically or mechanically deployable mini-bridges, inflatable balloons or synthetic muscles. The surgical procedure comprises using a ciliary muscle relaxant to stretch the lens/zonules/ciliary muscle assembly. An ultrasonic biomicroscope (UBM) is then used to enable the surgeon to see the area for implantation and the mini-bridges and thus perform endoscopic or incisional surgery to implant the mini-bridges in and around zonular cavities.

1 Claim, 15 Drawing Sheets

U.S. PATENT DOCUMENTS

| | | |
|---|---|---|
| 5,258,025 A | 11/1993 | Fedorov et al. |
| 5,275,623 A | 1/1994 | Sarfarazi |
| 5,300,118 A | 4/1994 | Silvestrini et al. |
| 5,354,331 A | 10/1994 | Schachar |
| 5,389,222 A | 2/1995 | Shahinpoor |
| 5,465,737 A | 11/1995 | Schachar |
| 5,476,514 A | 12/1995 | Cumming |
| 5,489,299 A | 2/1996 | Schachar |
| 5,496,366 A | 3/1996 | Cumming |
| 5,503,165 A | 4/1996 | Schachar |
| 5,529,076 A | 6/1996 | Schachar |
| 5,578,081 A | 11/1996 | McDonald |
| 5,674,282 A | 10/1997 | Cumming |
| 5,722,952 A | 3/1998 | Schachar |
| 5,735,607 A | 4/1998 | Shahinpoor |
| 5,766,171 A | 6/1998 | Silvestrini |
| 5,782,894 A | 7/1998 | Israel |
| 5,821,664 A | 10/1998 | Shahinpoor |
| 5,824,086 A | 10/1998 | Silvestrini |
| 5,843,188 A | 12/1998 | McDonald |
| 5,888,243 A | 3/1999 | Silvestrini |
| 6,006,756 A | 12/1999 | Shadduck |
| 6,007,578 A | 12/1999 | Schachar |
| 6,013,101 A | 1/2000 | Israel |
| 6,051,023 A | 4/2000 | Kilmer et al. |
| 6,051,024 A | 4/2000 | Cumming |
| 6,096,077 A * | 8/2000 | Callahan et al. ............ 623/6.18 |
| 6,494,910 B1 * | 12/2002 | Ganem et al. ............... 623/4.1 |
| 6,506,212 B1 * | 1/2003 | Zhou et al. ................ 623/6.38 |
| 6,692,524 B1 * | 2/2004 | Baikoff ........................ 623/4.1 |
| 2004/0260395 A1 * | 12/2004 | Boxer Wachler ............ 623/4.1 |

FOREIGN PATENT DOCUMENTS

| | | | |
|---|---|---|---|
| CH | 681687 A5 * | 5/1993 | |
| FR | 2794965 A1 * | 12/2000 | |
| FR | 2837694 A1 * | 10/2003 | |
| WO | WO 00/40174 A1 * | 7/2000 | |
| WO | WO 2004010904 A1 * | 2/2004 | |

OTHER PUBLICATIONS

Schachar (Schachar RA, Anderson DA., "The mechanism of ciliary muscle function" Ann Ophthalmol. 1995; 27:126-132.

Schachar RA., "Histology of the ciliary muscle-zonular connections", Ann Ophthalmol. 1996; 28:70-79).

* cited by examiner

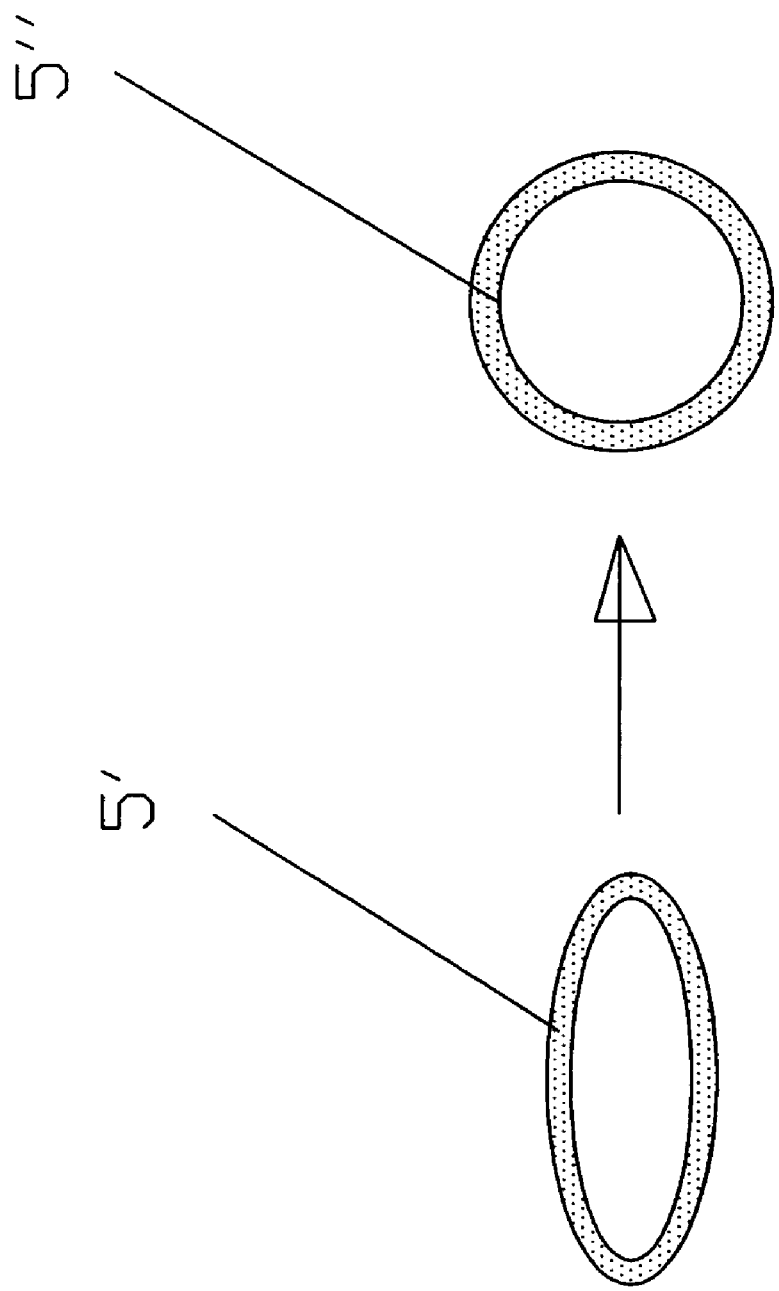

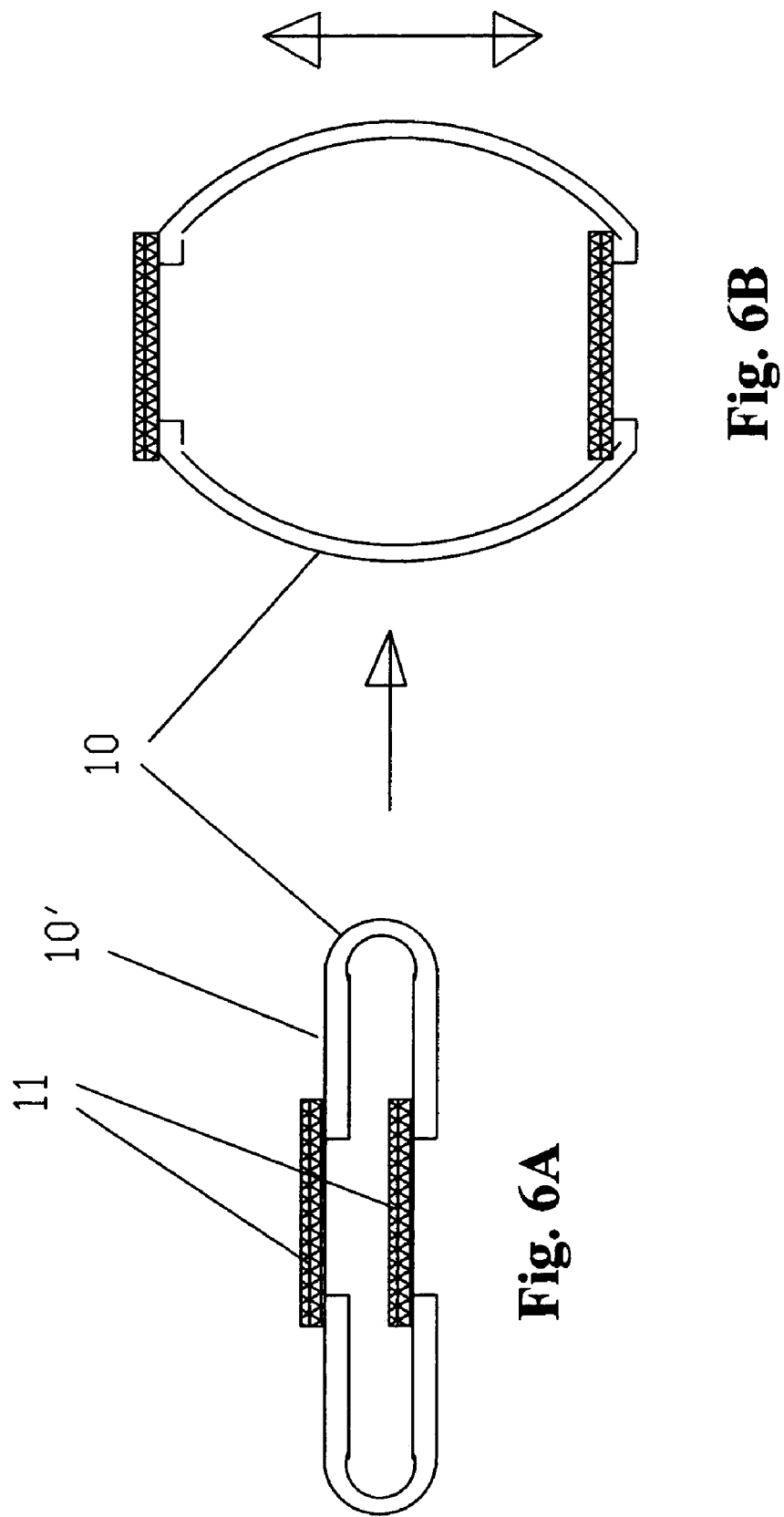

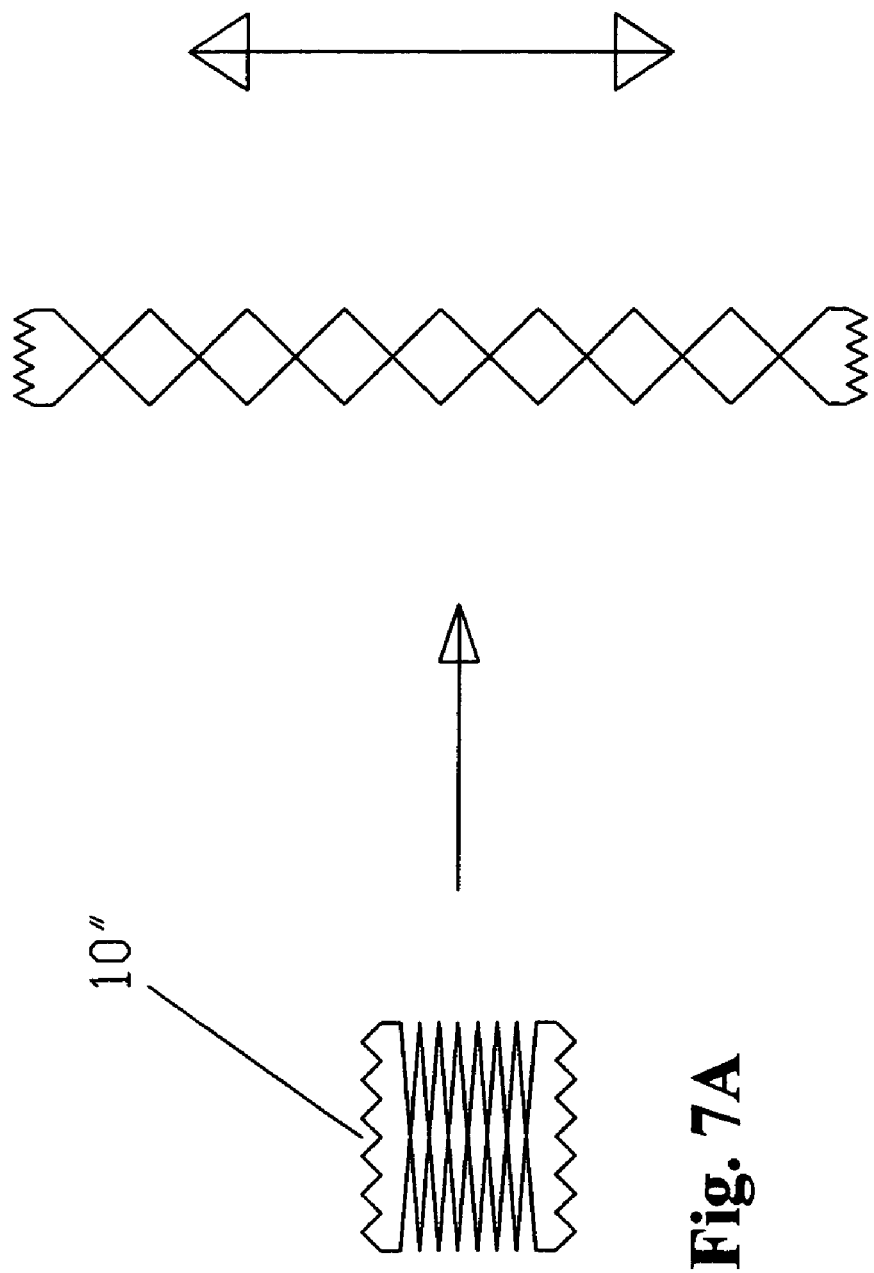

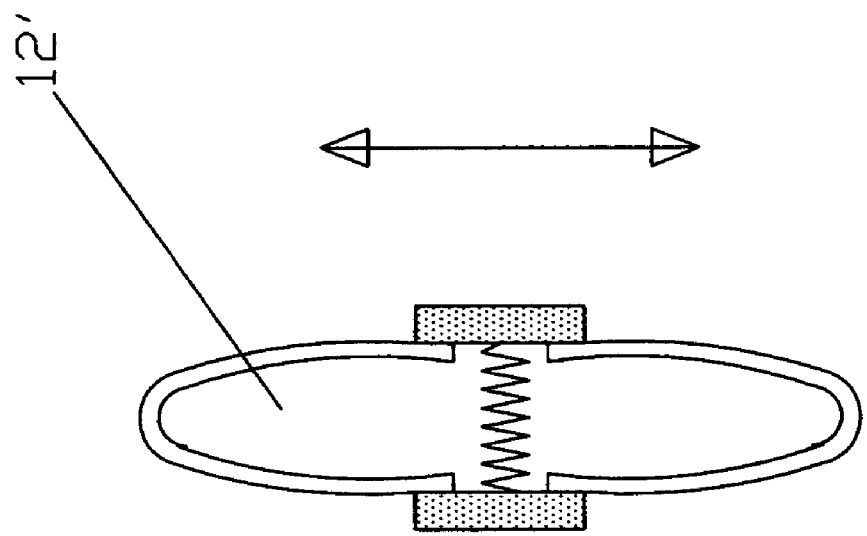
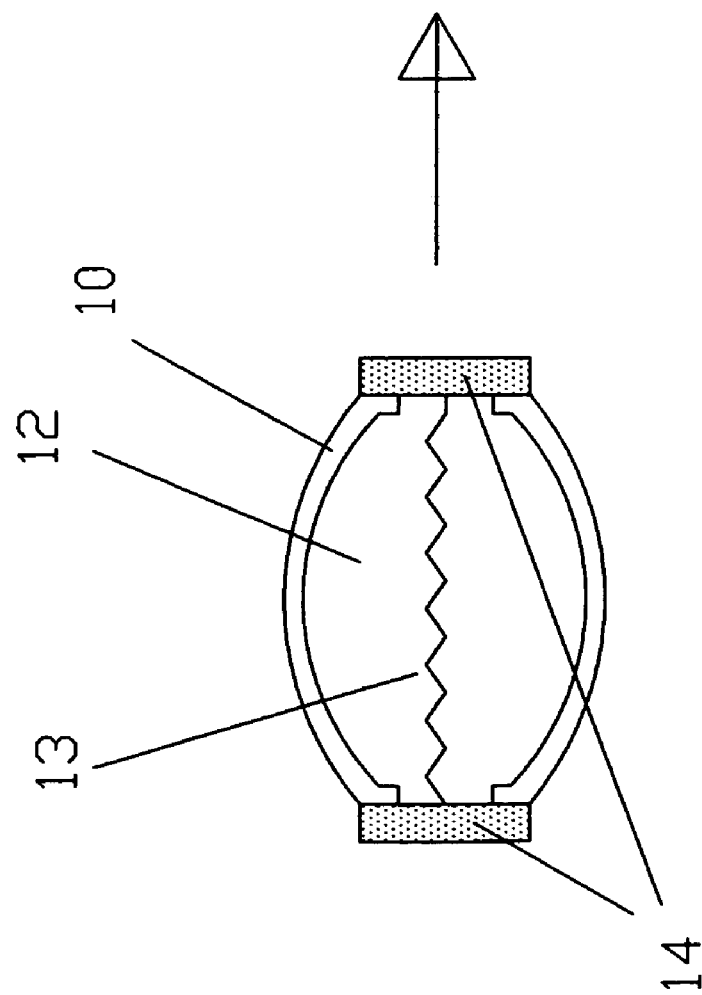
Fig. 8A
Fig. 8B

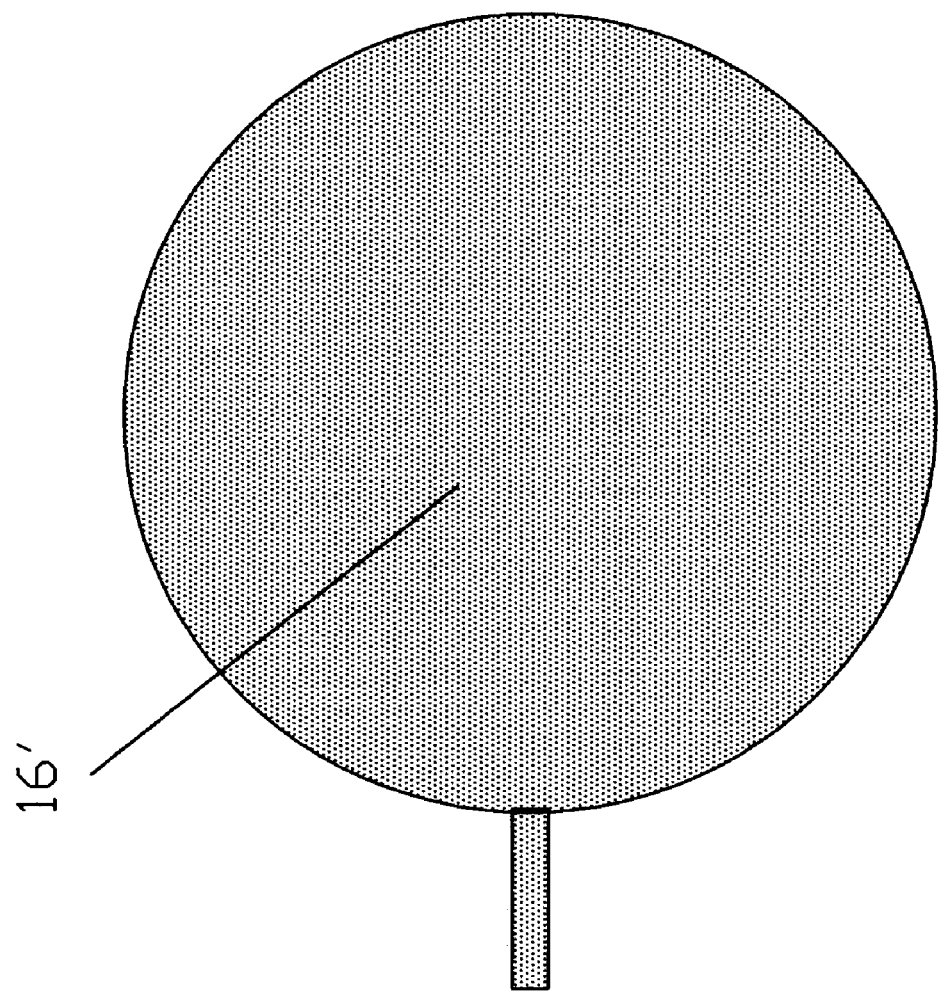
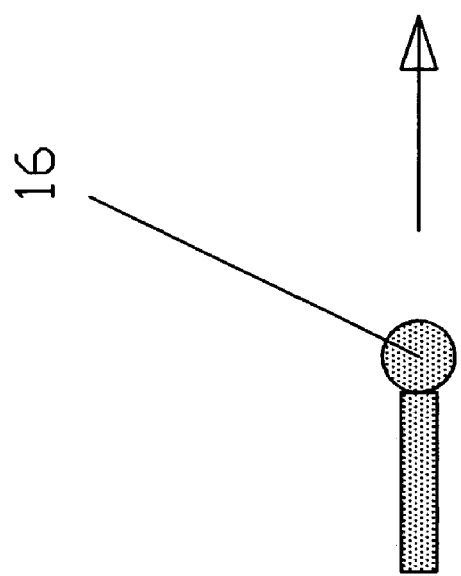
Fig. 10A
Fig. 10B

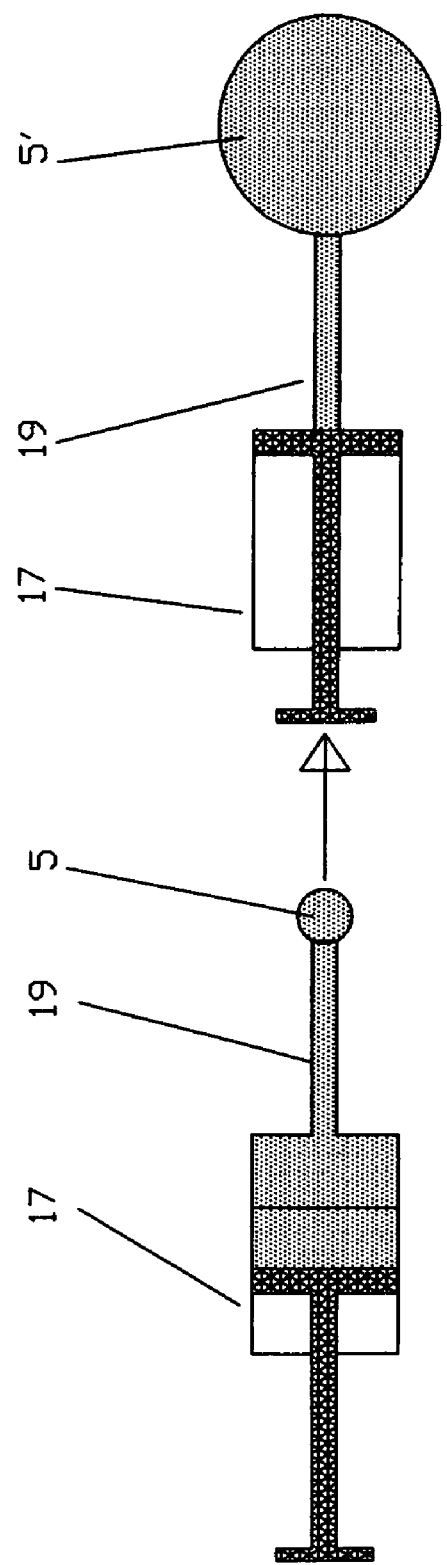

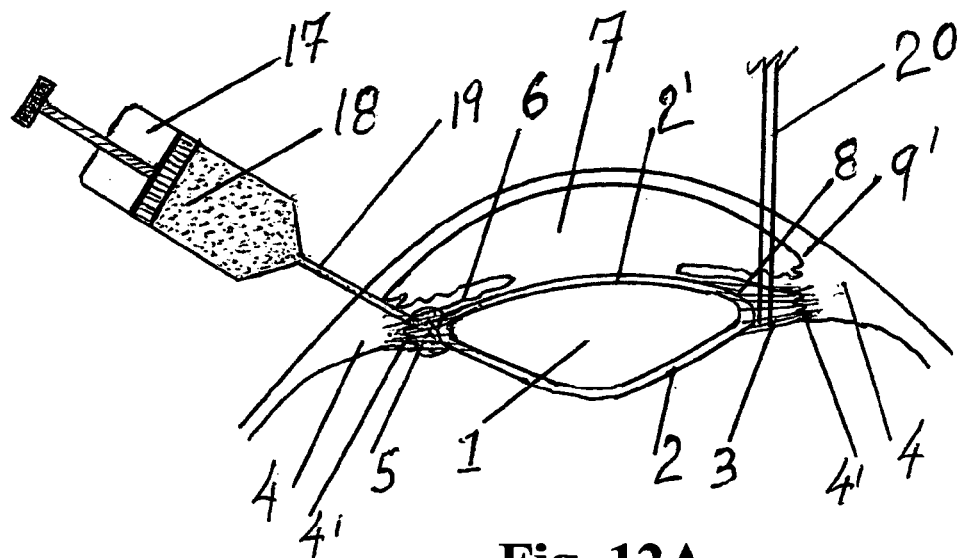
Fig. 12A
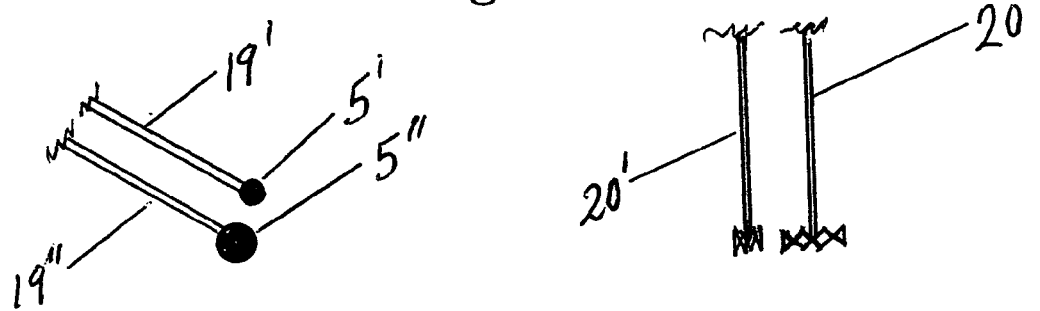
Fig. 12B
Fig. 12C

ACCOMMODATING ZONULAR MINI-BRIDGE IMPLANTS

CROSS-REFERENCE TO RELATED APPLICATIONS

This application is based on U.S. Provisional Application Ser. No. 60/223,141 entitled "Surgical Correction of Presbyopia By Synthetic Muscle Bridge Implants (Virtual Reading Glasses)" filed on Aug. 7, 2000, the teachings of which are incorporated herein by reference.

BACKGROUND OF THE INVENTION

1. Field of the Invention (Technical Field)

The invention relates to an apparatus and method for surgical correction of presbyopia and hyperopia and more particularly to surgical corrections for near vision accommodation of the natural eye lens by the contraction of ciliary muscle/zonule assembly.

2. Background Art

Normally the human eye loses its ability to focus on nearby objects as individuals reach the age of 40. This condition, known as presbyopia, is due to a progressive loss in the elasticity of the lens of the eye. This is caused by the ciliary muscle which can no longer exert the necessary changes in the lens' shape. Normally the ciliary muscle forces the lens in a rounded shape through the action of zonule fibers on the lens capsule to accommodate for viewing near objects.

The conventional optometric solution to the problem of presbyopia is a prescription of reading glasses or, for individuals who already require glasses to correct other refractive errors such as myopia or astigmatism, a prescription of bifocal or multifocal glasses. This is the reason that Benjamin Franklin invented bifocals in 1760. This century has witnessed a revolution in the surgical treatment of ophthalmic disorders and refractive errors of the human eye. For example, some of these treatments include corneal implantations, cataract extraction, phacoemulsification of the lens, intraocular lens implantation, glaucoma implants to control the intraocular pressure, radial keratotomy, excimer laser ablation of the cornea, trabeculoplasty, iridotomy, virectomy, and the surgical buckle treatment for retinal detachment. The recent surgical solutions for myopia, hyperopia and astigmatism are laser photorefractive keratectomy (PRK), LASIK (laser-assisted in-situ keratomileusis) and RK or radial keratotomy. Modern techniques for correction of human eye refractive errors are corneal implants (Intacs, Keravision rings), scleral implants (SASI, Schachar Accommodative Scleral Implants) and smart constricting bands equipped with artificial muscle structures to change the eye length.

The effective focal length of the human eye must be adjusted to keep the image of the object focused as sharply as possible on the retina. This change in effective focal length is known as accommodation, and is accomplished in the eye by varying the shape of the crystalline lens. This is necessary for the human eye to have clear vision of objects at different distances. Generally speaking, in unaccommodated normal vision, the curvature of the lens is such that distant objects are sharply imaged on the retina/macula. In the unaccommodated vision, close objects are not sharply focused on the retina/macula and their images lie behind the retinal surface. In order to visualize a near object clearly, the curvature of the crystalline lens is increased, thereby increasing its refractive power and causing the image of the near object to fall on the retina/macula/fovea region. The change in shape of the crystalline lens is accomplished by the action of ciliary muscle/zonule assembly by which, according to the classical theory of accommodation by German Scientist von Helmholtz (von Helmholtz H.,"Uber die akkommodation des auges", Albrecht von Graefef Arch Ophthalmol, 1855; 1:1–89), the radial tension in the lens is reduced allowing the lens to becomes more convex. In the unaccommodated human eye the lens and its capsule are suspended on the optical axis behind the pupil by a circular assembly of radially directed collagenous fibers called the zonules of Zinn. The inner ends of the zonules are attached to the lens capsule and the outer ends are attached to the ciliary body. The ciliary body is a muscular constricting ring of tissue located just within the outer supporting structure, or sclera of the eye. The ciliary muscle is relaxed in the unaccommodated eye and therefore assumes its largest inner diameter. According to the Helmholtz theory, the relatively large diameter of the ciliary body in this unaccommodated condition causes a tension on the zonules which in turn pull radially outward on the lens capsule, making it less convex. In this state, the refractive power of the lens is relatively low and the eye is focused for clear vision of distant objects. When the eye is focused on a near object, the muscles of the ciliary body contract. This contraction causes the ciliary body to move forward and inward, thereby relaxing the outward pull of the zonules on the equator of the lens capsule and reducing the zonular tension on the lens. This allows the elastic capsule of the lens to contract causing an increase in the sphericity or convexity of the lens, resulting in an increase in the optical refraction power of the lens. Therefore, according to Helmholtz's theory, when an individual focused his eye for near vision his ciliary muscle in the eye contracted and released tension on the lens zonular ligaments allowing the lens to elastically rebound and thicken by itself. In a way the theory asserts that the natural stress-free state of the lens is when the ciliary muscle contracts and releases the tension in the zonules to allow the lens to relax back to its natural state, which is more convex and spherical.

Recently, Schachar (Schachar R A, Anderson D A.,"The mechanism of ciliary muscle function'" Ann Ophthalmol. 1995; 27:126–132; and Schachar R A.,"Histology of the ciliary muscle-zonular connections", Ann Ophthalmol. 1996; 28:70–79.) has proposed a radically different theory of accommodation. The fundamental departure, according to Schachar, from the classical Helmholtz theory is that the tension in the zonule fibers is constant and that the lens capsule itself grows in time, by about 20 microns a year, to finally reduce the tension in the zonules enough to make the action of the ciliary muscle contraction less effective on the lens itself. Schachar further maintains that the hardening of the lens with time individually differs for people when they reach the approximate age of 40, while getting presbyopic is almost universal for people of 40 years old, and thus, is not the only reason behind the phenomenon of presbyopia. By the time one reaches the age of 40, the lens has increased sufficiently in size so that the ciliary muscles can no longer exert tension through the equatorial, anterior, and posterior zonular fibers of the lens when the ciliary muscle contracts for accommodation. For this reason, he maintains, one loses the ability to accommodate at approximately the age of 40 and experience progressive loss of near vision as one gets older. Schachar theorizes that presbyopia could be corrected if the ciliary muscles could be stretched a small amount to allow them to function on the lens. Relatively recently the Schachar Accommodative Scleral Implant (SASI) has been developed. By making a small incision in the outer coat of the eye (the sclera), one can place a small polymethylmethacrylate (PMMA)) arched stent within this scleral tunnel which will exert a stretching effect on the equatorial lens fibers. Four of these are placed around the eye in the sclera (approximately 2 mm away from the cornea), and approximately 90 degrees apart. These stents are designed to allow restoration of accommodation. From the Schachar hypothesis of accommodation it could be deduced that if one were able to increase the distance between the lens equator and the ciliary muscle, one could again stretch the zonules and reverse the effect of lens growth and to narrow this distance.

There are several prior art devices and methods in the form of implants and prostheses for the surgical correction of presbyopia, hyperopia, and myopia.

U.S. Pat. No. 5,354,331 to Schachar discloses how presbyopia and hyperopia are treated by a method that increases the amplitude of accommodation by increasing the effective working distance of the ciliary muscle in the presbyopic eye. This is accomplished by expanding the sclera in the region of the ciliary body. A relatively rigid band having a diameter slightly greater than that of the sclera in that region is sutured to the sclera in the region of the ciliary body. The scleral expansion band comprises anterior and posterior rims and a web extending between the rims, the anterior rim having a smaller diameter than the posterior rim.

In U.S. Pat. No. 5,465,737 to Schachar the teachings are similar to those of the '331 patent, except that the expansion of the sclera is accomplished by suturing to the sclera a relatively rigid band having a diameter slightly greater than that of the sclera in the region of the ciliary body, by weakening the sclera overlying the ciliary body, by surgical procedures or treatment with enzymes, heat or radiation, whereby intraocular pressure expands the weakened sclera, or by surgical alloplasty.

U.S. Pat. Nos. 5,489,299; 5,722,952; 5,503,165; and 5,529,076 to Schachar report essentially the same ideas as U.S. Pat. Nos. 5,354,331 and 5,465,737 with some improvements such that presbyopia and hyperopia are treated by a method that increases the amplitude of accommodation by increasing the effective working distance of the ciliary muscle in the presbyopic eye.

U.S. Pat. No. 6,007,578 to Schachar discloses how presbyopia is treated by implanting within a plurality of elongated pockets formed in the tissue of the sclera of the eye, a prosthesis having an elongated base member having an inward surface adapted to be placed against the inward wall of the pocket, and having a ridge on the inward surface of the base extending along at least a major portion of the major dimension of the base. The combined effect of the implanted prostheses is to exert a radially outward traction on the sclera in the region overlying the ciliary body, which expands the sclera in the affected region together with the underlying ciliary body.

U.S. Pat. No. 6,006,756 to Shadduck discloses a system and technique called magnetoresonant induction of an intrastromal implant that is adapted for corneal re-shaping. The technique is utilized to correct mild to high hyperopia and presbyopia by steepening the anterior corneal curvature in a single treatment, or in periodic treatments over the lifetime of the patient.

U.S. Pat. No. 5,147,284 to Fedorov, et al., teaches a device for restoration of visual functions in cases of affected optic nerve and retina with an electromagnetic field radiator emitting the latter field into the region of the eyeball and an electromagnetic field receiver adapted to interact with the radiator, both of them exerting an electrostimulation effect on the optic nerve and the retina.

U.S. Pat. No. 5,782,894 to Israel discloses a device and method for treating presbyopia by which the ciliary muscles of the eyes are electrically stimulated when the internal rectus muscles of the eyes are activated in order to focus the eyes on objects within the near field of vision.

U.S. Pat. No. 4,961,744 to Kilmer, et al., discloses a surgical apparatus for inserting a plastic, split end, adjusting ring into the stroma of the cornea of the eye wherein the adjusting ring includes, as a part thereof, a dissecting head to part the stroma and provide a pathway for the adjusting ring as the ring is rotated.

U.S. Pat. No. 5,300,118 to Silvestrini, et al., discloses an intrastromal corneal ring (ICR) that is adjustable in thickness and has an elongated, flexible, preferably transparent or translucent body which forms a circle.

U.S. Pat. No. 5,824,086 to Silvestrini discloses a preformed intrastromal corneal insert. It is made of a physiologically compatible polymer and may be used to adjust corneal curvature and thereby correct vision abnormalities.

U.S. Pat. No. 6,051,023 to Kilmer, et al., discloses a surgical apparatus for inserting a plastic, split end, adjusting ring into the stroma of the cornea of the eye which includes a dissecting head to part the stroma and provide a pathway for the adjusting ring as the ring is rotated.

U.S. Pat. No. 5,888,243 to Silvestrini discloses an intrastromal corneal ring housing comprising at least one outer layer of a physiologically compatible polymer having a low modulus of elasticity. The inner portion of the hybrid intrastromal corneal ring may be hollow or may contain one or more physiologically compatible polymers.

U.S. Pat. No. 5,766,171 to Silvestrini teaches a device and procedure for the correction of optical abnormalities in a human eye. It involves use of an inventive electrosurgical energy probe with specific physical configurations. The process preferably utilizes a high frequency RF electrodesiccation or ablation device. The procedure involves the initial step of forming at least one access site allowing access to the corneal volume behind the Bowman's Layer. It preferably is placed in the anterior surface of the cornea through and ending posterior to the Bowman's layer of the eye. The electrosurgical probe is then introduced into the access site and, depending upon the visual abnormality to be corrected, the probe is activated to adjust the volume of the corneal stromal layers through ablation or desiccation. The shape of the volume desiccated or ablated is dependent upon the aberration to be corrected.

A number of proposals have been made for changing the focal length of the implanted intraocular lens for cataract patients in response to the natural accommodation mechanism of the eye. One type of adaptive lens comprises an artificial lens whose shape is changed in response to the contraction and expansion of the ciliary muscle. This type of lens is disclosed in U.S. Pat. No. 4,254,509 to Tennant, which teaches an eye implant which has an optical lens anteriorly convex and posteriorly planar supported on two diametrically opposed coplanar feet through two supporting members forming an arch. Each supporting member is unitary with the lens and rooted in one of the feet outside the perimeter of the lens to support the lens with the posterior thereof anterior to the plane of the feet. The lens is formed of a rigid biologically inert material. The supporting members are formed of soft biologically supporting material. The resulting structure, when fixed into the sclera of the eye, will change as to move the lens anteriorly when forces are applied to the feet upon contraction of the ciliary body.

Similar ideas have been disclosed by U.S. Pat. No. 4,842,601 to Smith, U.S. Pat. No. 4,888,012 to Horn, et al., and U.S. Pat. No. 4,253,199 to Banko. Two other types of adaptive lenses are described in U.S. Pat. No. 4,994,082 to Richards, et al., and U.S. Pat. No. 5,275,623 to Sarfarazi shows a similar type of compound adaptive lens.

U.S. Pat. No. 4,892,543 to Turley describes a compound system comprising a fixed lens having curved posterior and anterior surfaces and a second component, which is positioned axially posterior of the lens.

U.S. Pat. No. 4,790,847 to Woods, U.S. Pat. No. 5,152,789 to Willis, and U.S. Pat. No. 4,409,691 to Levy describe adaptive lens systems utilizing a simple intraocular lens. These systems have focusing capabilities, which are achieved by axially shifting the lens in response to normal contraction and expansion of the ciliary muscle resulting from changes in range between the eye and an object under observation. These patents describe similar systems for providing motion of the lens. In each case the ciliary muscle controls zonules, which in turn provide tension to a lens capsule in which the lens system is mounted. The extremities of the capsule press against a radially compelled, spring-like structure, which also forms a relatively large angle of somewhat, less than 90° with the optical axis of the eye. The lens is positioned on the optical axis. Relaxation of the ciliary muscle releases the radial force and allows the spring to form a more nearly flat shape. When the ciliary muscle contracts, the pressure on the spring is increased by the action of the lens capsule, the angle between the spring and the optical axis is decreased, and the lens moves axially away from the ciliary muscle.

U.S. Pat. No. 4,765,329 to Cumming and Redwitz discusses an intraocular lens insertion instrument for the implantation of intraocular lenses into the human eyes. The instrument is particularly intended for use in conjunction with the insertion of deformable intraocular lenses through extremely small incisions.

U.S. Pat. No. 6,051,024 to Cumming teaches intraocular lenses for implanting within natural capsular bags of human eyes that have features on distal end portions to prevent movement or sliding thereof relative to fibrosis pockets or tunnels defined about proximally adjacent haptic portions to fixate haptics against dislocation.

U.S. Pat. No. 5,578,081 to McDonald presents an artificial lens unit insertable into a capsular eye lens zone from which a natural lens has been removed, comprising the lens having a light refracting optical portion defining an axis, and consisting of plastic; the unit including haptics for positioning the lens in the capsular zone, the haptics extending at angles relative to a plane normal to the axis and passing through the lens; and the haptics' angles characterized in that the lens is displaced in the direction of the axis by the haptics in response to eye muscle constriction of the periphery of the capsular zone toward the axis.

U.S. Pat. No. 4,786,445 to Portnoy and Ting teaches a method of attaching a fixation member to an optic comprising providing the optic with a cavity opening adjacent the peripheral edge of the optic with a shoulder in the cavity, inserting an inner end portion of the fixation member into the cavity, transmitting laser energy through the optic to the inner end portion of the fixation member to cause the inner end portion to become flowable, and allowing the flowable portion of the fixation member to harden and interlock with the shoulder to resist withdrawal of the fixation member from the cavity.

U.S. Pat. No. 5,843,188 to McDonald teaches a method of providing an artificial lens inserted into the eye between the iris and the natural lens zone. McDonald discloses an artificial lens to be compliant and to have anterior and posterior surfaces, and haptics extending away from the periphery of the artificial lens. The artificial lens is inserted to extend into position between the iris and the zone, and to cause the haptics to extend into adjacency to the ciliary muscles, and allows the haptics to adhere to the ciliary muscles. Subsequent movement of the ciliary muscles causes movement of the haptics transmitted to effect bodily movement of the lens in posterior and anterior directions to change the angularity of refraction of light passing through the lens toward the eye retina.

U.S. Pat. No. 5,476,514 to Cumming, U.S. Pat. No. 5,496,366 to Cumming and U.S. Pat. No. 5,674,282 to Cumming teach an accommodating intraocular lens to be implanted within the natural capsular bag of a human eye from which the natural lens matrix has been removed through an anterior capsulotomy in the bag circumferentially surrounded by a capsular remnant. During a postoperative healing period following surgery, the anterior capsular remnant fuses to the posterior capsule of the bag by fibrosis about haptics on the implanted lens, and the lens is deflected rearwardly to a distant vision position against the elastic posterior capsule of the bag in which the posterior capsule is stretched rearwardly. After fibrosis is complete, natural brain-induced contraction and relaxation of the ciliary muscle relaxes and stretches the fused remnant and increases and reduces vitreous pressure in the eye to effect vision accommodation by the fused remnant, the posterior capsule, and vitreous pressure. A method of utilizing the intraocular lens in a human eye to provide the eye with accommodation and to enable utilization of a lens with a relatively large optic.

U.S. Pat. No. 5,258,025 to Fedorov, Zuev, and Aznabaev presents an optical body, a positioning element, and a supporting element are shaped as an integral unit and have the same radius of curvature that provides for full adherence of the integral unit to an intact natural lens. The distance between the diametrically opposite portions of the supporting element is at least equal to the distance between Zinn's zonules on which the corrective lens rests.

U.S. Pat. No. 6,013,101 to Israel teaches an intraocular lens assembly for implantation in a human eye, the eye including a ciliary muscle and zonules controlled by the ciliary muscle, the assembly including an optic, having anterior and posterior surfaces depending from a common edge, at least two, preferably rigid, linkage arms, each being attached to the optic at a first position on the arm thereof, and cooperating with ciliary muscle or the zonules at a second position on the arm, and at least two pivots, one of which is rotatably attached to each respective linkage arm intermediate the first and second positions.

U.S. Pat. No. 5,108,429 to Wiley teaches an adjustable focus lens apparatus which includes a transparent lens body having a periphery, an attachment device adjacent to the periphery of the lens body for mounting the lens apparatus in an eye, and a plurality of micromotor devices spaced equally about and connected between the periphery of the lens body and the attachment means, each of the micromotor devices being responsive to an external control signal for selectively changing the position of an associated portion of the lens body with respect to the cornea and retina so that the functional power and astigmatism of the lens can be appropriately adjusted.

It is clear from the above patent literature search that no prior art has considered the possibility of accommodating the natural eye lens or intraocular lens with mini-bridges placed outside the eye natural capsule and particularly within the canal of Hannover, a space between the anterior zonular membrane and the posterior zonular membrane, the equatorial zonules and the ciliary muscle to restore natural eye lens accommodation by the contraction of ciliary muscle in near vision situation.

SUMMARY OF THE INVENTION
(DISCLOSURE OF THE INVENTION)

In accordance with the present invention there is provided a method and apparatus for surgical correction of presbyopia and hyperopia by the use of mini-bridges for contraction of the eye lens on demand. It also teaches surgical restoration of near vision accommodation to the natural eye lens by the contraction of ciliary muscle/zonule assembly. A circularly distributed assembly of directly pressure transmitting, zonule fiber-reinforced active mini-bridges is surgically placed between the interior surfaces of the ciliary muscle and the exterior equatorial surface of the natural eye lens capsule. Accordingly, the present invention provides a novel method and apparatus for restoring natural accommodation to the natural eye lens utilizing one or more mini-bridges which transmit the circularly distributed contraction force of the ciliary muscle to the natural lens capsule. This restores natural near vision accommodation, to correct presbyopia and hyperopia on demand. The present invention circularly and symmetrically squeezes the eye lens through the lens capsule by means of radially distributed pressure transmitting mini-bridges when the ciliary muscle contracts in close vision situations, in such a way to actively perform near vision accommodation by changing the curvature of the eye lens. The surgical procedure proposed first uses a ciliary muscle relaxant to create a taut configuration for the lens/zonules/ciliary muscle assembly and then employs an ultrasonic biomicroscope (UBM) and endoscopic or incisional surgery to place such mini-bridge implants in and around zonular cavities, such as, preferably the canal of Hannover so that the two ends of the mini-bridges span the internal surfaces of the ciliary muscle to the exterior surface of the natural eye capsule. The surgeon, during this surgical placement of mini-bridges continuously observes the microscopic details of the ciliary muscle, zonules, lens capsule and the Hannover canal.

The composite synthetic muscles to be used for the mini-bridges are either passive biocompatible mini-bridges made with polymeric gels such as polyacrylamide, polymethylmethacrylate (PMMA), polypropylene or silicone polymers or a composite of them, electromagnetically or mechanically deployable structural mini-bridges, liquid or gas inflatable mini-balloons or biocompatible synthetic muscles such as electroactive ionic polymeric artificial muscle structures, active materials such as preferably piezocerams, piezopolymers, electroactive and eletrostrictive polymers, magnetostrictive materials, liquid crystal elastomers, and electro or magnetorheological materials suitably electroded with biocompatible metals such as gold, platinum and titanium and thermally deployable shape memory alloy (SMA) or shape memory polymers (SMP) structures. The passive form of polymeric mini-bridges may also be light curable to enable the surgeon to implant them in liquid form by incisional tools and light cure them to a solid form in-situ.

A primary object of the present invention is to restore natural near vision accommodation to a presbyopic or hyperopic eye.

Another object of the present invention is to enable presbyopes and hyperopes to become emmetropes (normal vision).

Yet another object of the present invention is to enable cataract patients to accommodate their implanted intraocular lenses for near and far vision after surgery by the natural contraction and relaxation of their ciliary muscles.

Yet another object of the present invention is to enable presbyopes and hyperopes to see near objects without the use of glasses.

A primary advantage of the present invention is that it enables a presbyopic or hyperopic eye to use its own ciliary muscle contraction force to restore natural near vision accommodation.

Yet another advantage of the present invention is that it enables cataract patients, after surgical placement of their intraocular lenses, to accommodate or focus on near and far objects by the natural contraction and relaxation of their ciliary muscles.

Yet another advantage of the present invention is that it employs a simple surgical procedure for the placement of mini-bridges which involves minimally invasive endoscopic or incisional tools to place the mini-bridge implants.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 5(a) shows the pre-surgical configuration of a thermally deployable mini-bridge made up of shape memory alloy (SMA) or shape memory polymer (SMP).

FIG. 5(b) shows the post surgical configuration of a thermally deployable mini-bridge made up of shape memory alloy (SMA) or shape memory polymer (SMP).

FIG. 6(a) shows the pre-surgical configuration of an electrically deployable mini-bridge made up of ionic polymeric artificial muscle materials.

FIG. 6(b) shows the post surgical configuration of an electrically deployable mini-bridge made up of ionic polymeric artificial muscle materials.

FIG. 7(a) shows the pre-surgical configuration of a mechanically deployable mini-bridge made up of a lazy tong-like (scissor-like) deployable structure that can be endoscopically implanted and deployed within the Hannover canal.

FIG. 7(b) shows the post surgical configuration of a mechanically deployable mini-bridge made up of a lazy tong-like (scissor-like) deployable structure that can be endoscopically implanted and deployed within the Hannover canal.

FIG. 8(a) shows the pre-surgical configuration of a deployable mini-bridge made up of an electroactively deployable ionic polymeric mini-bridge with bonded electrodes.

FIG. 8(b) shows the post surgical configuration of a deployable mini-bridge made up of an electroactively deployable ionic polymeric mini-bridge with bonded electrodes.

FIG. 10(a) shows the pre-surgical configuration of a deployable mini-bridge made up of a liquid or gas inflatable mini-balloon that can be endoscopically implanted.

FIG. 10(b) shows the post surgical configuration of a deployable mini-bridge made up of a liquid or gas inflatable mini-balloon that can be endoscopically implanted.

FIG. 11(a) shows the pre-surgical configuration of a softly resilient mini-bridge made up of an elastically deformable and implantable material made with polymethylmethacrylate (PMMA), polypropylene, silicone or other polymeric soft materials.

FIG. 11(b) shows the post surgical configuration of a softly resilient mini-bridge made up of an elastically deformable and implantable material made with polymethylmethacrylate (PMMA), polypropylene, silicone or other polymeric soft materials.

FIG. 12(a) shows the preferred embodiment for surgical implantation of mini-bridges by means of a syringe or an incisional endoscope.

FIG. 12(b) shows the general configuration of the tip of the syringe for implantation of the mini-bridges.

FIG. 12(c) shows the preferred incisional endoscope to deploy and implant the mini-bridges.

Figure 1B:
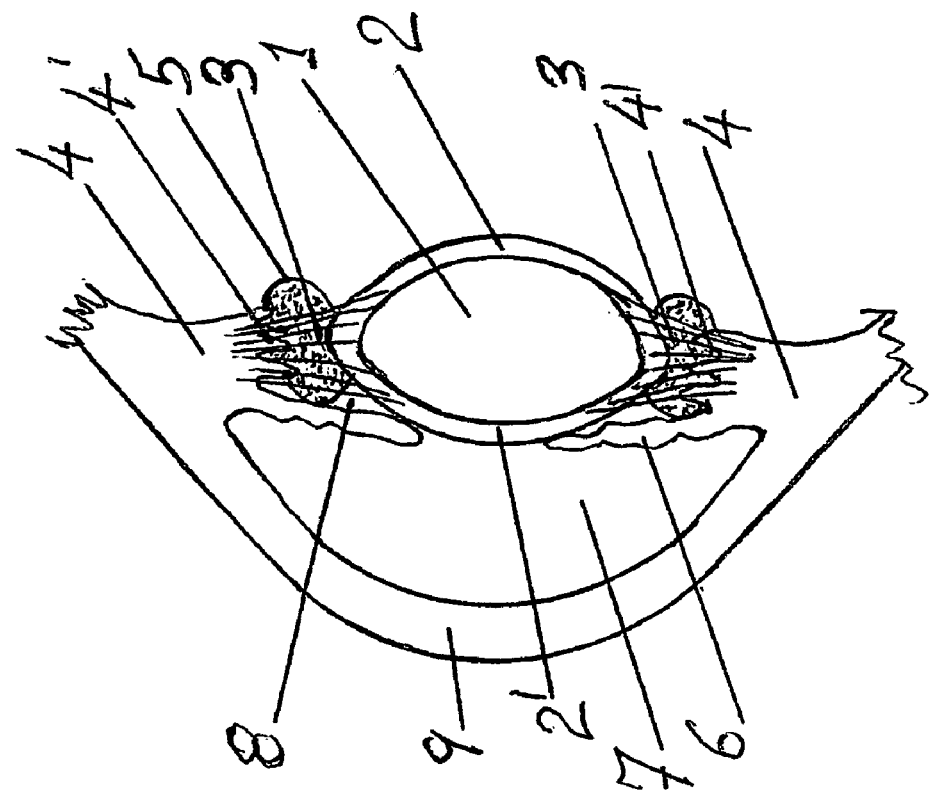
FIG. 1(b) shows the side view of FIG. 1(a) in an accommodated or contracted state.

DESCRIPTION OF THE PREFERRED EMBODIMENTS (BEST MODES FOR CARRYING OUT THE INVENTION)

A novel theory of accommodation and surgical correction of presbyopia and hyperopia is first presented, which is a unified theory of accommodation. This theory serves as the foundation for the present invention. There is credible evidence that Helmholtz was right in claiming that some loss of elasticity and/or sclerosis does occur in the lens and the lens capsule with age. In addition, it is accepted that the lens itself is ectodermal and grows equatorially at a rate of approximately 20 microns per year. Consequently, it will be harder for the lens to elastically deform back to its more spherical state either naturally or by the application of hoop pressure on its capsule. It is also theorized that the zonular filaments are never loose and lax because that would render the lens dynamically unstable, such as in sports activities requiring rapid postural changes of the head or the body or in the absence of gravity in space. Therefore, the zonular filaments are always under compression like the filaments in a soft hairbrush. If one considers a bundle of soft hairs in a soft hair brush, one can easily observe that although individual hair can not take much compression because they simply buckle or collapse, but collectively as a bundle they can sustain condiderable compressive pressures. If a hand is placed on a soft hairbrush one can easily feel the compressive resistance of the hair bundle or hair filaments collectively. This example is similar to the zonular fibers and shows that they are under compression rather than tension when engaged in accommodation. From this theory, an effective surgical procedure to correct presbyopia can be constructed. It is further maintained, that the most relaxed and natural state of the eye is when one is looking at distant objects. In this state the ciliary muscle is relaxed and almost stress-free, the zonules are relaxed and almost stress free, with a small amount of compressive force or hoop pressure applied to them by the ciliary muscle. Most important, is that the lens and the lens capsules are relaxed and almost stress free. Any other state of the eye is an accommodative state in which the ciliary muscle is exerting a hoop stress on the lens capsule through compressive action of the zonular filaments. With progressive hardening and the loss of elasticity of the lens, and its ectodermal growth it will become harder and harder for the ciliary muscle to accommodate by contraction. This is because, on the one hand, the lens and the lens capsule are harder to deform, and on the other hand, the growth of the lens causes the zonular filaments to buckle as they press against the ciliary body. Thus, zonules in this bent and buckled state cannot directly transmit the constricting force of the ciliary muscle to the lens capsule. Referring to the hairbrush example, if the hand on the hairbrush bristles is squeezed down, there is a stronger distributed force or pressure resisting against compression. However, as the downward pressure increases, the hairbrush hair bristles collectively buckle and/or collapse and the compressive force or pressure decreases and it will become easier to further deform the brush bundle. Thus, the best solution is to create direct pressure transmission bridges between the ciliary muscle and the lens capsule so that upon contraction of the ciliary muscle, the hoop pressure is directly transmitted to the anterior region of the lens capsule and thus forces the lens to become more spherical, and accommodate for near vision.

The present invention describes elements that operate as force transmitting bridges, to transmit the contraction force of ciliary muscles to the lens capsule. A circularly distributed assembly of them works together to constrict circularly the lens capsule to accomplish the task of accommodation or making the lens more spherical. All the user has to do is to look at near objects which causes the ciliary muscle to contract and thus push the bridges which in turn push the capsule. On demand, in this invention, means mental demand because as soon as one wants to look at near objects, the ciliary muscle being a smooth voluntary muscle, contracts and with the mini-bridges, accentuates natural accommodation, making the lens more spherical than without the mini-bridges.

Figure 1A:
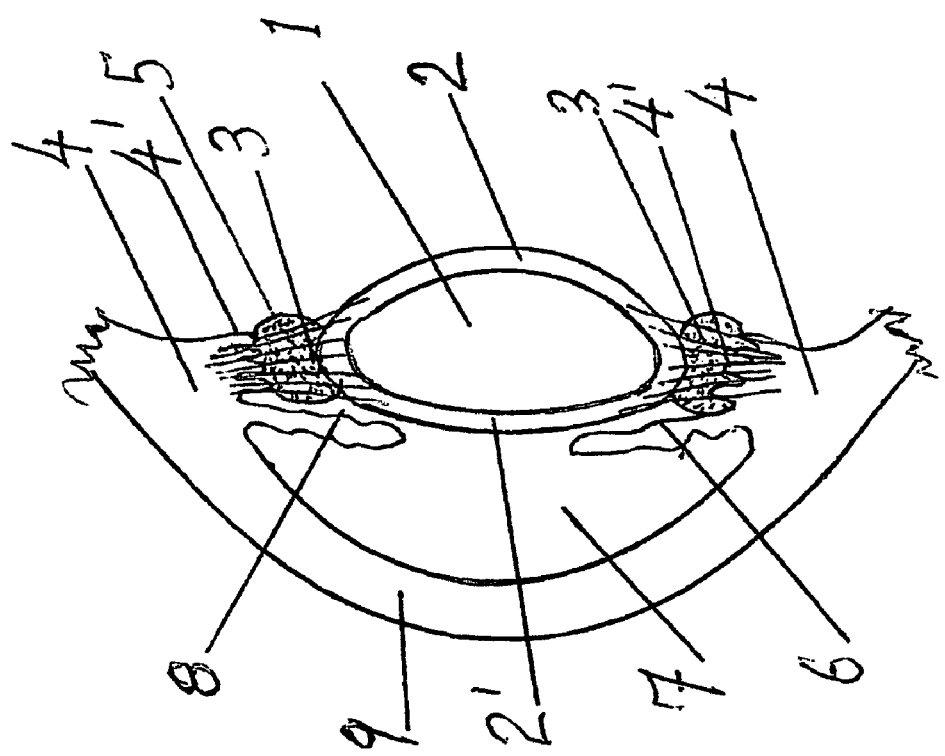
FIG. 1(a) shows a side view of the eye lens and its capsule attached circumferentially to the zonular fibers, which are in turn attached to the ciliary muscle in an unaccommodated or relaxed state.

FIG. 1(a) depicts a partial side view of the eye lens 1 and its capsule (anterior capsule 2' and posterior capsule 2) attached circumferentially to the zonular fibers 3, which are in turn attached to the ciliary muscle 4 in an unaccommodated or relaxed state in the presence of iris 6, anterior chamber 7, posterior chamber 8, and cornea 9. The implanted mini-bridges 5, which are zonule fiber-reinforced composite materials are bridging and transmitting force between the equatorial surface of the lens capsule 2 and the exterior surfaces of ciliary muscle 4 and processes 4'. The mini-bridges 5 are preferably composite synthetic muscles which are either preferably passive biocompatible mini-bridges made with water-based polymer hydrogels such as polyacrylamide, polymethylmethacrylate (PMMA), polypropylene or silicone polymers or light curable polymeric melts or a composite of them, liquid or gas inflatable mini-balloons, deployable structural mini-bridges such as deployable lazy tong structures, or biocompatible synthetic muscles such as electroactive ionic polymeric artificial muscle structures, active materials such as preferably piezo-cerams, piezopolymers, electroactive, and eletrostrictive polymers, magnetostrictive materials, liquid crystal elastomers, and electro or magnetorheological materials suitably electroded with biocompatible metals such as gold, platinum, and titanium, and thermally deployable shape memory alloy (SMA) or shape memory polymers (SMP) structures. The detailed working of these elements will be described later in this section. However, it must be mentioned here that all these mini-bridge implants, upon placement in the preferably Hannover canal, work like force transmitting bridges or load bearing walls. Thus, they transmit the contraction force of a ciliary muscle to the equatorial region of the corresponding lens capsule. A circularly distributed assembly of these mini-bridges works together to constrict the lens capsule circularly to accomplish the task of accommodation or making the lens more convex or spherical. All the user has to do is to want to see near objects, in which case his or her ciliary muscles contract naturally to accommodate for near vision.

FIG. 1(b) shows the same partial side view of the eye lens 1 and its capsule (anterior capsule 2' and posterior capsule 2) attached circumferentially to the zonular fibers 3, which are in turn attached to the ciliary muscle 4 in an accommodated or contracted state in the presence of iris 6, anterior chamber 7, posterior chamber 8, and cornea 9. The mini-bridges 5, which are zonule fiber-reinforced composite materials are bridging and transmitting force between the equatorial surface of the lens capsule 2 and the exterior surfaces of ciliary muscle 4 and processes 4'. Note from FIGS. 1(a) and 1(b) that upon contraction of the ciliary muscle 4 in near vision situations, which is caused by the user desire to see near objects, the contraction force is directly transmitted through the mini-bridges 5 to the equatorial exterior surfaces of the capsule 2, which in turn causes the lens 1 to accommodate in near vision, by becoming more spherical or convex.

Figure 2B:
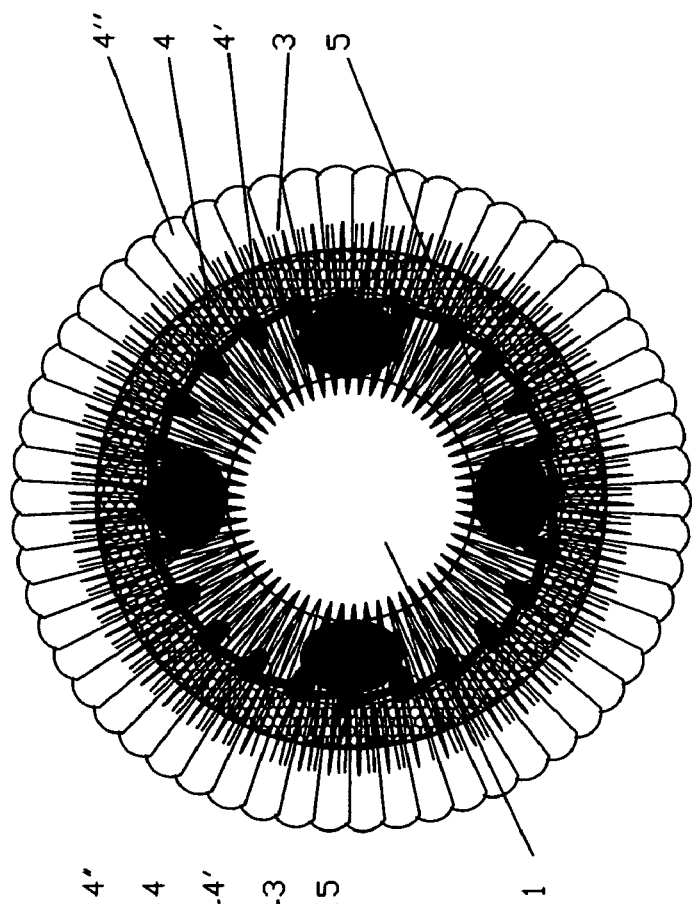
FIG. 2(b) shows a front view of FIG. 1(b).
Figure 2A:
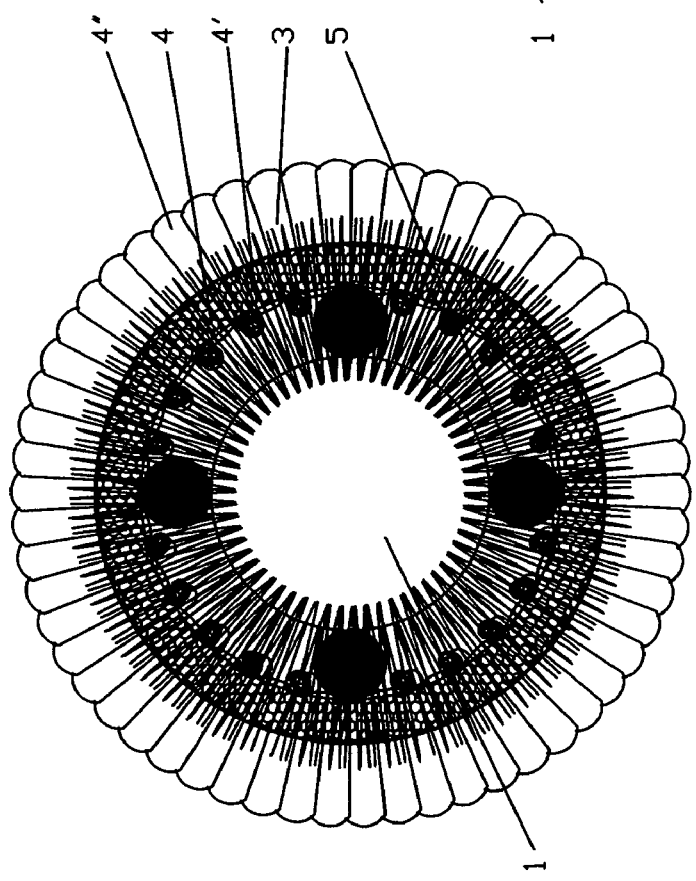
FIG. 2(a) shows a front view of FIG. 1(a).

FIG. 2(a) is a front view of FIG. 1(a) and shows the eye lens 1 and its capsule attached circumferentially to the zonular fibers 3, which are in turn attached to the ciliary muscle 4 and in the presence of ciliary processes 4' protruding in to the zonular fibers 3 in an unaccommodated or relaxed state in the presence of ora serrata region 4". The four mini-bridges 5, which are zonule fiber-reinforced composite materials are bridging and capable of transmitting force between the equatorial surface of the lens capsule 2 and the exterior surfaces of ciliary muscle 4 and processes 4'. In this relaxed and unaccommodated state, no ciliary muscle contraction force is transmitted to the lens capsule and the eye is in a normal distant vision relaxed state and the ciliary muscle is in a relaxed state.

FIG. 2(b) shows the same front view of FIG. 2(a) in an accommodated or contracted state in the presence of ora serrata region 4". Note from FIGS. 2(a) and 2(b) that upon contraction of the ciliary muscle 4 in near vision situations, the contraction force, which is a circularly distributed hoop force, is directly transmitted through the mini-bridges 5 to the equatorial exterior surfaces of the capsule 2, which in turn causes the eye lens 1 to become more convex and to accommodate in near vision.

Figure 3A:
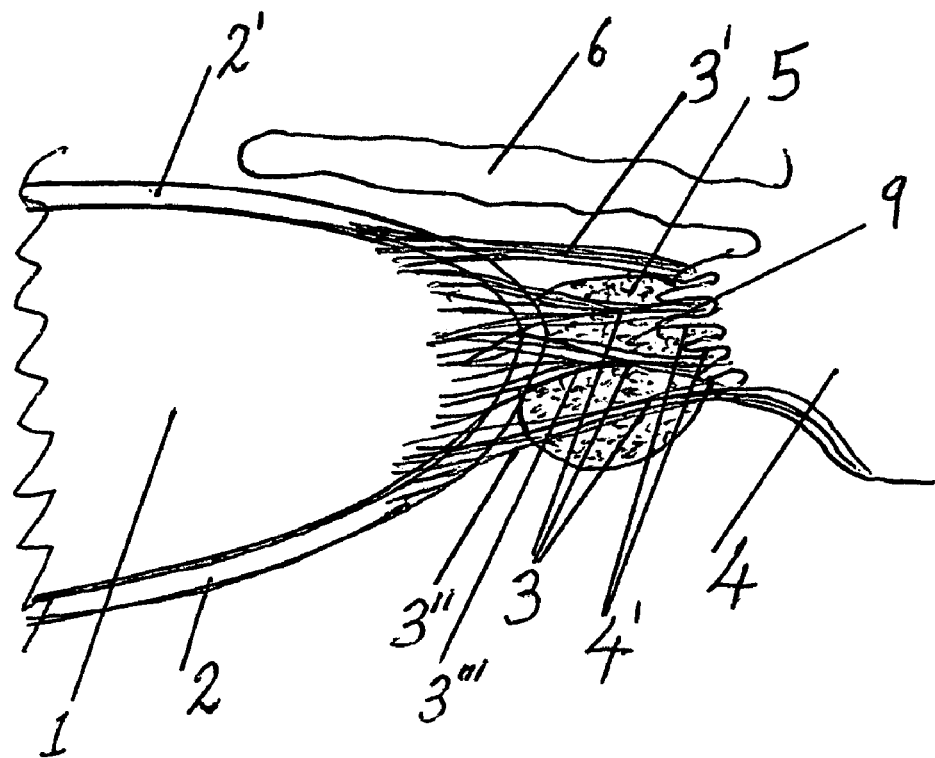
FIG. 3(a) shows a close-up view of the eye lens and its capsule attached circumferentially to the zonular fibers of FIG. 1(a).

FIG. 3(a) is a close-up side view of FIG. 1(a) showing the eye lens 1 and its capsule 2 attached circumferentially to the zonular fibers 3, 3', 3" and 3''', which are in turn attached to the ciliary muscle 4 and in the presence of ciliary processes 4' protruding in to the zonular fibers 3 in an unaccommodated or relaxed state in the presence of the iris 6, posterior and anterior capsules 2 and 2', respectively and the Hannover canal 9 which is the space between the anterior zonules 3' and posterior zonules 3" and encompassing the equatorial zonules 3'''. In this relaxed and unaccommodated state, no ciliary muscle contraction force is transmitted to the lens capsule and the eye is in a normal distant vision relaxed state and the ciliary muscle is in a relaxed state.

Figure 3B:
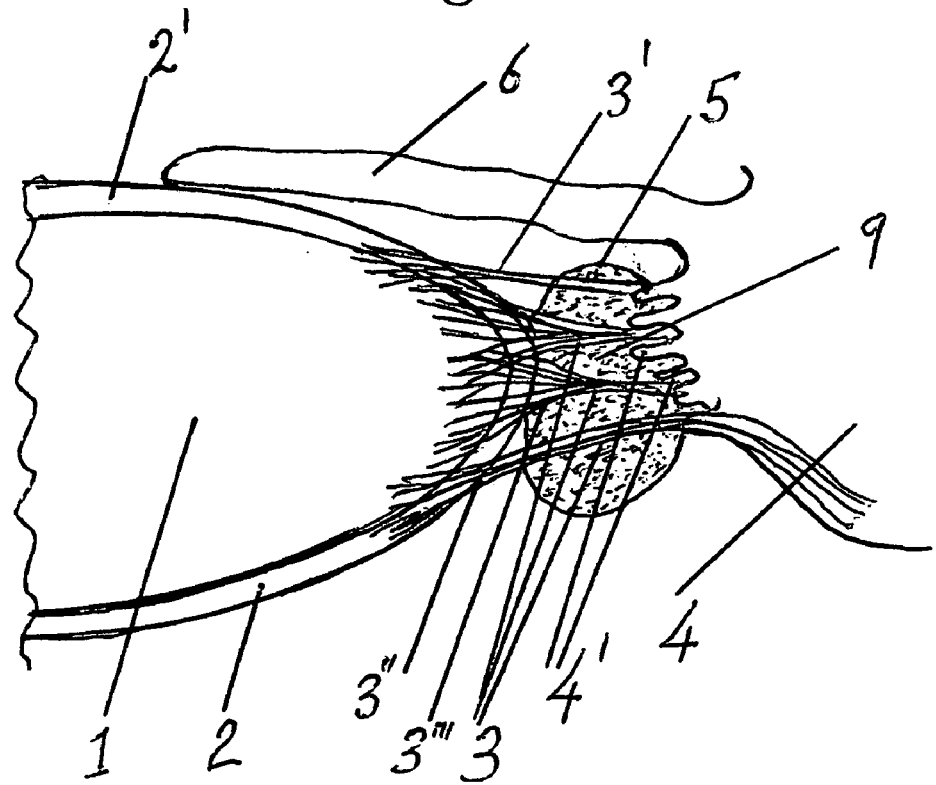
FIG. 3(b) shows a close-up side view of the eye lens and its capsule attached circumferentially to the zonular fibers of FIG. 1(b).
Figure 3A:
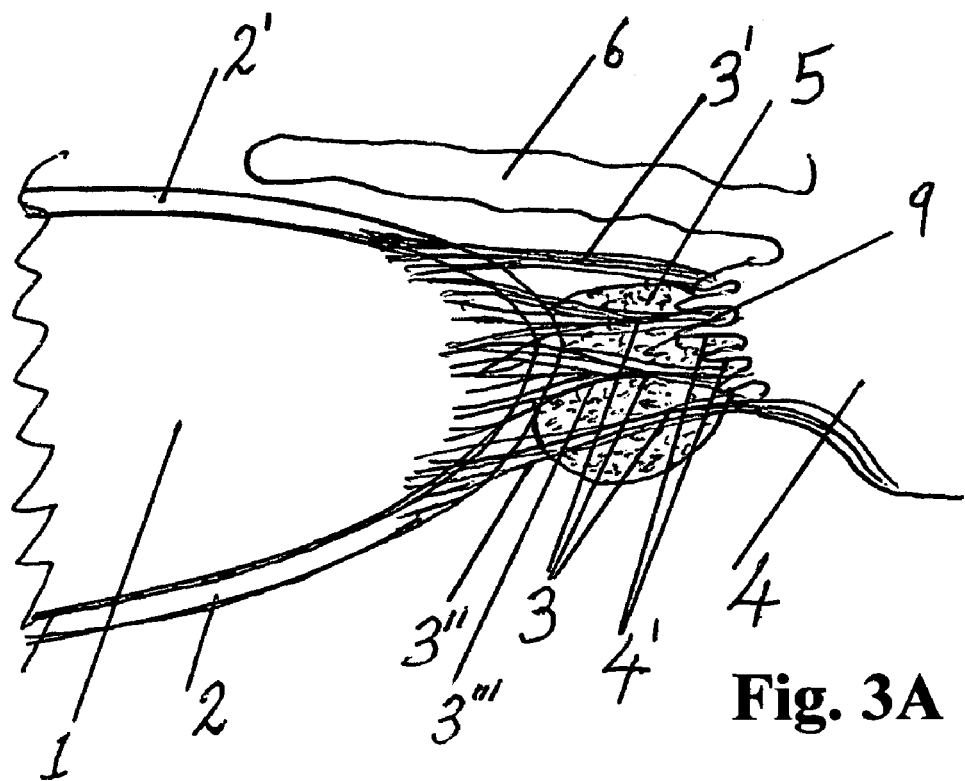
Figure 3B:
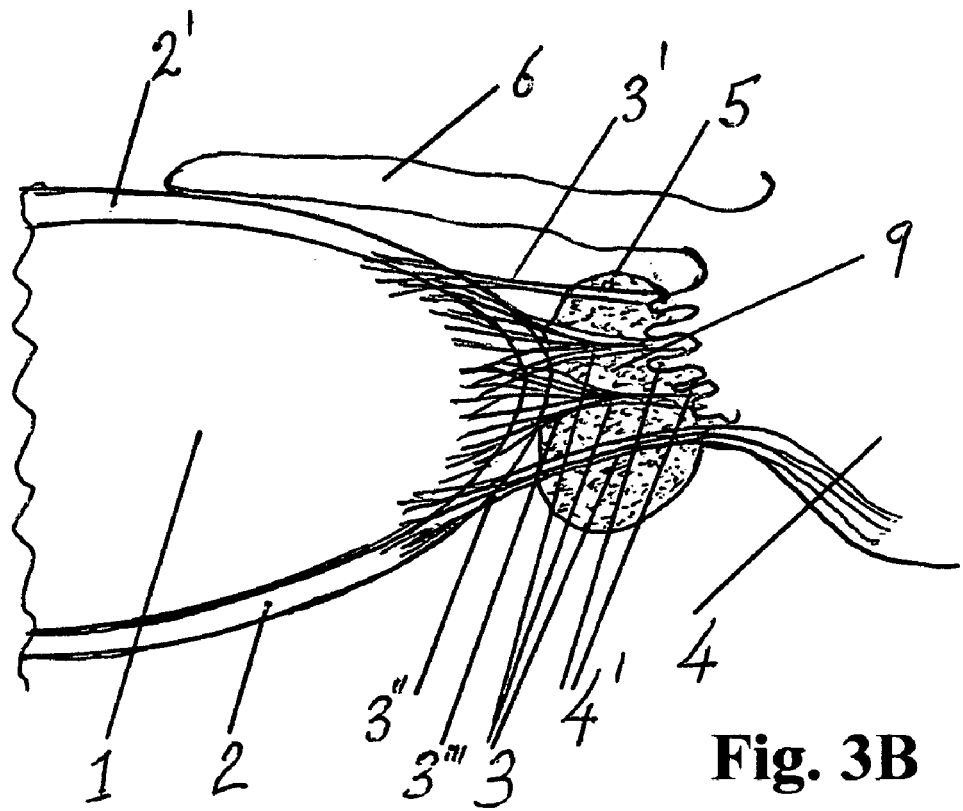

FIG. 3(b) depicts the same close-up side view as in FIG. 3(a) in an accommodated or contracted state. Note that in this accommodated state, upon contraction of the ciliary muscle 4 and ciliary processes 4' in near vision situations the contraction force, which is a circularly distributed hoop force, is directly transmitted through the mini-bridges 5 to the equatorial exterior surfaces of the capsule 2, which in turn causes the eye lens 1 to become more convex and to accommodate in near vision.

Figure 4A:
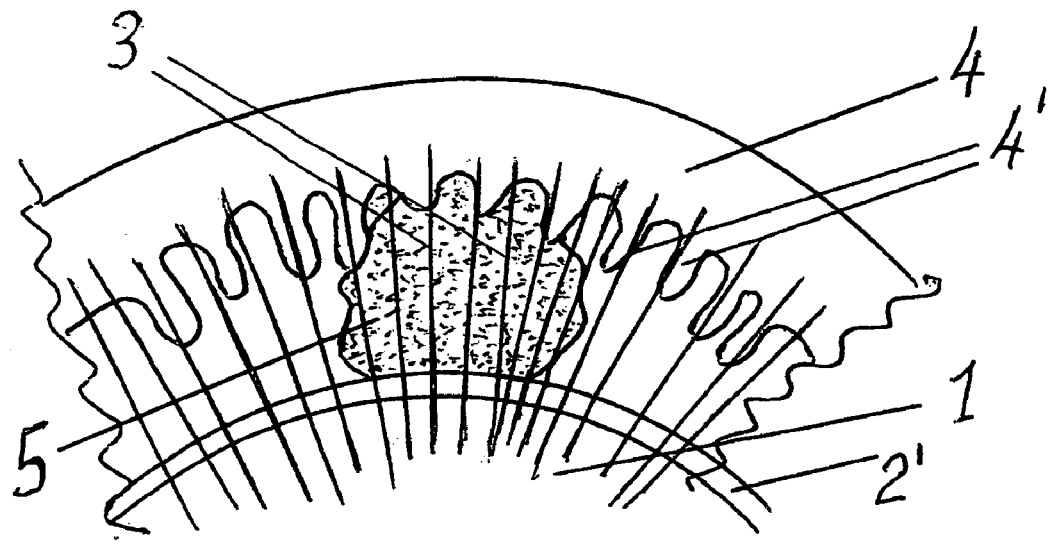
FIG. 4(a) shows a close-up front view of the eye lens and its capsule attached circumferentially to the zonular fibers of FIG. 1(a).

FIG. 4(a) is a close-up partial front view of FIG. 1(a) showing the eye lens 1 and its capsule 2 attached circumferentially to the zonular fibers 3, which are in turn attached to the ciliary muscle 4 and in the presence of ciliary processes 4' protruding in to the zonular fibers 3 in an unaccommodated or relaxed state. In this relaxed and unaccommodated state, no ciliary muscle contraction force is transmitted to the lens capsule and the eye is in normal distant vision state and the ciliary muscle is in a relaxed state.

Figure 4B:
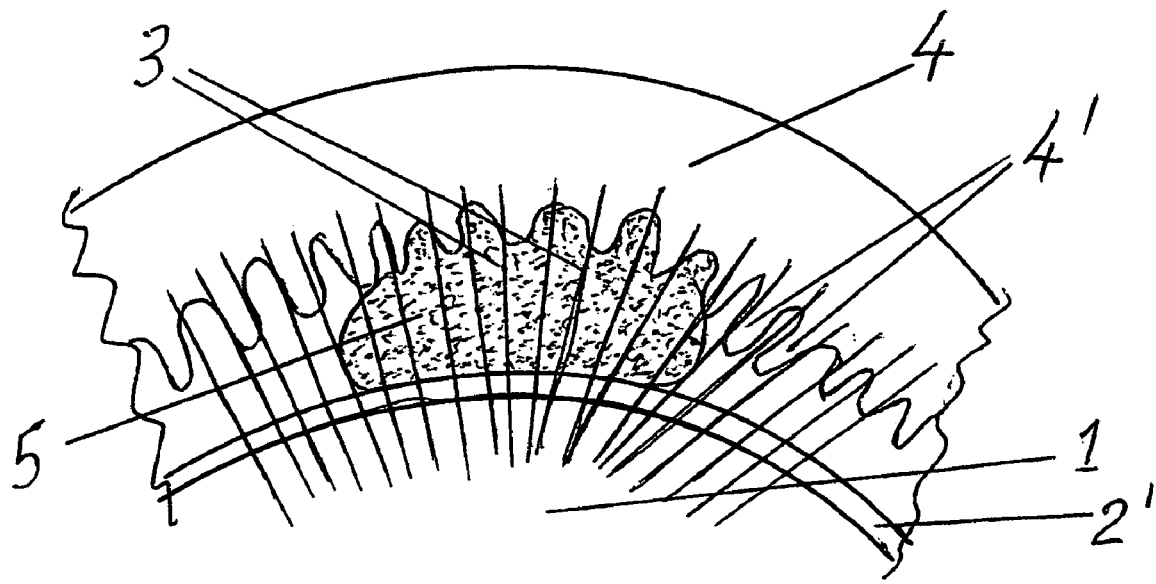
FIG. 4(b) shows a close-up front view of the eye lens and its capsule attached circumferentially to the zonular fibers of FIG. 1(b).

FIG. 4(b) depicts the same close-up partial front view as in FIG. 4(a) of the eye lens 1 and its capsule 2 attached circumferentially to the zonular fibers 3, which are in turn attached to the ciliary muscle 4 and in the presence of ciliary processes 4' protruding in to the zonular fibers 3 in an accommodated or contracted state. Note from FIGS. 4(a) and 4(b) that upon contraction of the ciliary muscle 4 in near vision situations the contraction force is directly transmitted through the mini-bridges 5 to the equatorial exterior surfaces of the capsule 2, which in turn causes the lens 1 to accommodate in near vision.

FIGS. 5, 6, 7, 8, 9, 10, 11, 12 and 13 depict a number of possible materials and configurations for the implantable and deployable mini-bridges 5.

FIG. 5(a) depicts a thermally deployable shape memory alloy (SMA) or shape memory polymer (SMP) mini-bridge implant 5' in a pre-transition state (soft state) which can be cooled by ice water and collapsed in to a thin slender column which can be endoscopically implanted in the Hannover canal. FIG. 5(b) shows the same implanted mini-bridge in activated and deployed configuration 5". This configuration is automatically achieved once the implant thermally equilibrate with body temperature and subsequently thermally deployed 5" with body temperature preferably within the Hannover canal to perform bridging action as well as transmitting force between the exterior surfaces of the ciliary muscle and ciliary processes and the equatorial surface of the eye capsule.

FIG. 6(a) depicts a mini-bridge made with electrically deployable ionic polymeric materials 10 in the form of a robotic mini-platform with appropriately attached electrodes 11 that can be transcutaneously deployed via an imbedded induction coil 10' to perform bridging action in a deployed configuration shown in FIG. 6(b). This embodiment also transmits a force between the exterior surfaces of the ciliary muscle and ciliary processes and the equatorial surface of the eye lens capsule. The ionic polymeric strips 10 reversibly bend under the action of an electric field.

FIG. 7(a) displays a lazy tong-like (scissor-like) deployable structure in a collapsed state 10" that can be endoscopically implanted and subsequently deployed, as shown in FIG. 7(b) within the Hannover canal to perform bridging action as well as transmitting force between the exterior surfaces of the ciliary muscle and ciliary processes and the equatorial surface of the eye lens capsule. This kind of mechanical deployment is performed endoscopically by scissor-like surgical tools.

FIG. 8(a) depicts an electroactively deployable ionic polymeric mini-bridge in a collapsed state 12 and deployed state 12', as shown in FIG. 8(b) with bonded electrodes 14 that can be transcutaneously deployed via an imbedded induction coil 13 and electroactive polymer strips 10, to perform bridging action as well as transmitting force between the exterior surfaces of the ciliary muscle and ciliary processes and the equatorial surface of the eye lens capsule. The ionic polymeric strips 10 reversibly bend under the action of an electric field.

Figure 9B:
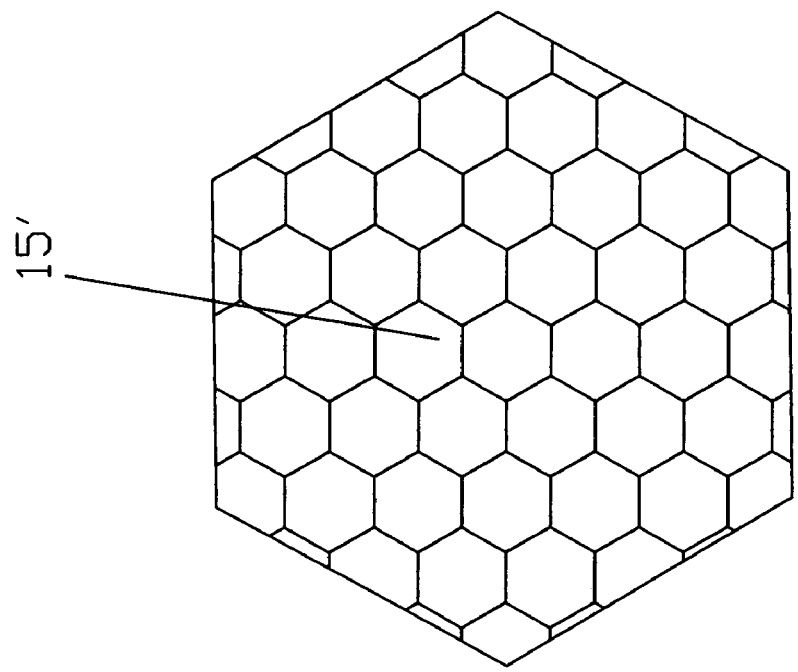
FIG. 9(b) shows the post surgical configuration of a deployable mini-bridge made up of a polymer hydrogel that can be implanted as a small solid grain in dry form in the canal of Hannover.
Figure 9A:
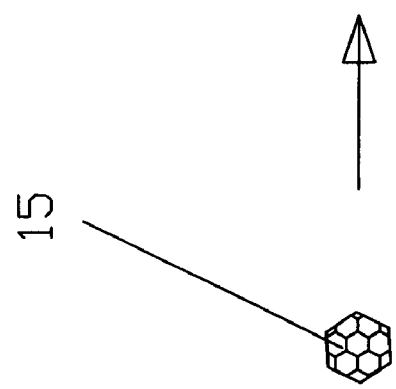
FIG. 9(a) shows the pre-surgical configuration of a deployable mini-bridge made up of a polymer hydrogel that can be implanted as a small solid grain in dry form in the canal of Hannover.

FIG. 9(a) depicts a polymer hydrogel that can be implanted endoscopically as a small solid grain 15 in dry form in the canal of Hannover. This grain 15 of polymer gel, such as polyacrylamide, will absorb enough aqueous humor and subsequently swell, about 1000 times its initial volume to deploy to a larger structure 15', as shown in FIG. 9(b), to perform bridging action as well as transmitting force between the exterior surfaces of the ciliary muscle and ciliary processes and the equatorial surface of the eye lens capsule. This particular mini-bridge implant is a highly preferred embodiment to perform the force bridging action between the contracted ciliary muscle and the lens capsule. This gel mini bridge upon swelling will be mostly filled with the aqueous humor and thus will be a natural element in the Hannover canal which in fact is a river bed or a canal for the circulation of aqueous humor in the eye. The gel mini-bridge upon swelling will naturally fill the space between the ciliary muscle and the capsule and will naturally intertwine with the zonular fibers.

FIG. 10(a) depicts a liquid or gas inflatable mini-balloon in a deflated state 16 and inflated state 16' as shown in FIG. 10(b). This mini balloon can be endoscopically implanted and subsequently inflated preferably within the Hannover canal to perform bridging action as well as transmitting force between the exterior surfaces of the ciliary muscle and ciliary processes and the equatorial surface of the eye lens capsule. Although the shape of the balloon in FIG. 10 is spherical, different balloon shapes can be utilized, for example cylindrical or multifingered shapes can be used (not shown).

FIGS. 11(a) and 11(b) depict elastically deformable and implantable mini-bridges 5 and 5' made with polymethylmethacrylate (PMMA), polypropylene, silicone polymer or other polymeric soft materials that can be injected, by means of a syringe 17 and a needle 19, in liquid form into the Hannover canal and subsequently enlarged and cured to a soft elastic mini-bridge 5 and 5'. Light curable polymeric melts are also included.

FIG. 12(a) depicts a partial side view of the configuration of the eye lens 1, ciliary muscle 4, ciliary processes 4', zonules 3, iris 6, the cornea/limbus region 9' and generally the posterior chamber 8. This is a preferred configuration for surgical implantation of mini-bridges by means of a syringe 17, needle 19 or an incisional endoscope 20. In this configuration the surgeon will use an ultrasonic biomicroscope to clearly see the ciliary muscle/zonules assembly, the endoscopic surgical tools and the Hannover canal on a TV monitor, or the like, during surgery, to either place or inject the mini-bridge material in to the Hannover canal by either a syringe 17 filled with the implantable material 18 to inject through the a needle 19 or an incisional endoscope 20.

FIGS. 12(b) and 12(c) display the general configuration of the tip (needle) of the syringe 19', 19" or incisional endoscope 20' and 20" to deploy and implant the mini-bridges 5' and 5" of the hydrogel, polymethylmethacrylate (PMMA), polypropylene, silicone polymer, light curable polymeric melts or deployable lazy tong-like mini-structures, respectively.

Figure 13:
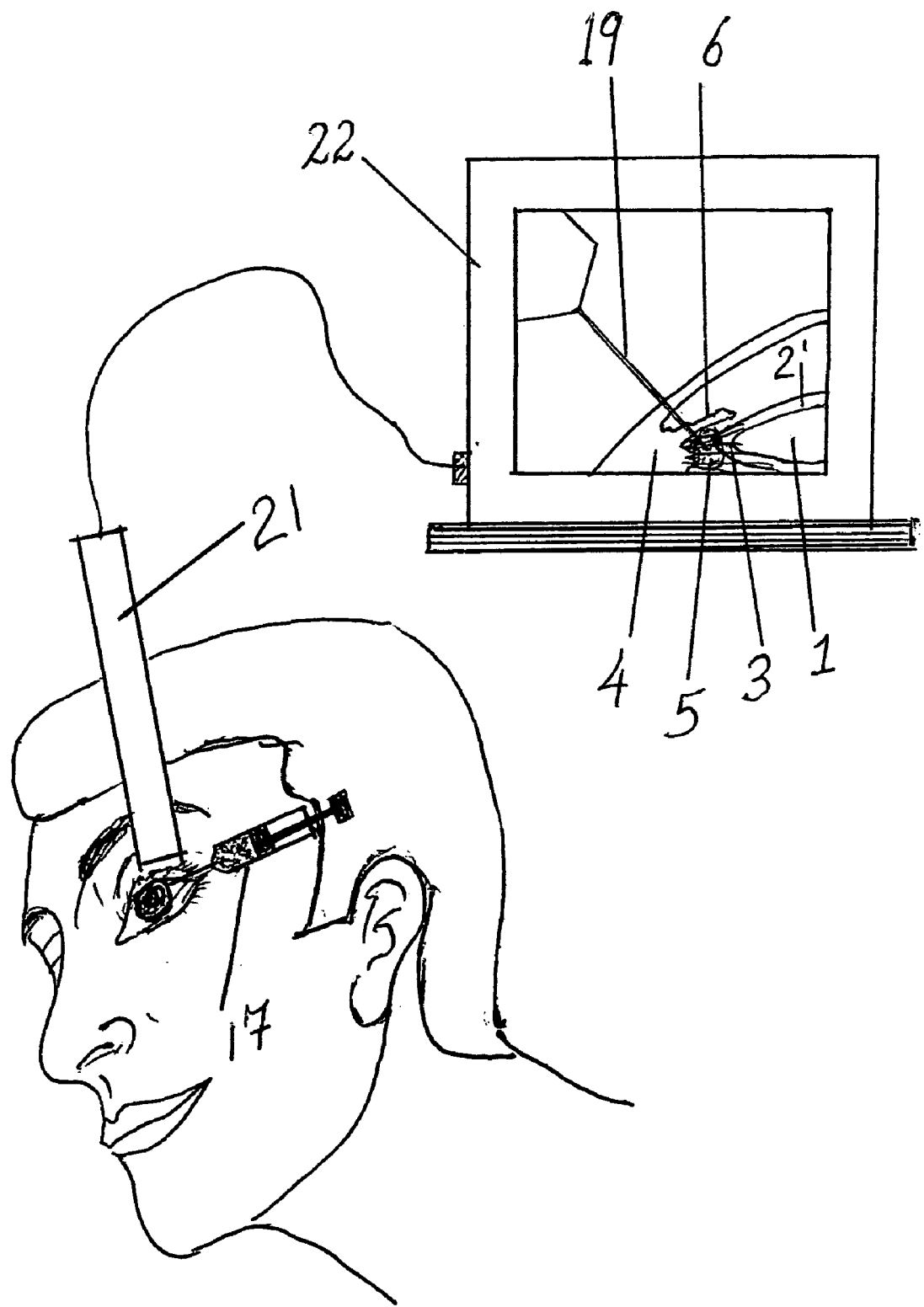
FIG. 13 depicts the general configuration for the surgical procedure employing an ultrasonic biomicroscope (UBM), a syringe or an incisional endoscope and a TV monitor to show the microscopic details of the ciliary/zonule assembly.

FIG. 13 depicts the general configuration for the surgical procedure employing an ultrasonic biomicroscope (UBM) 21 to enable the surgeon to clearly see the ciliary muscle 4/zonules 3/Hannover canal 9, lens 1, lens capsule 2', the iris 6 and endoscopic or incisional tools 19 on a TV monitor 22 while the surgeon places the mini-bridge implants by a syringe or an incisional endoscope 17.

Figure 14:
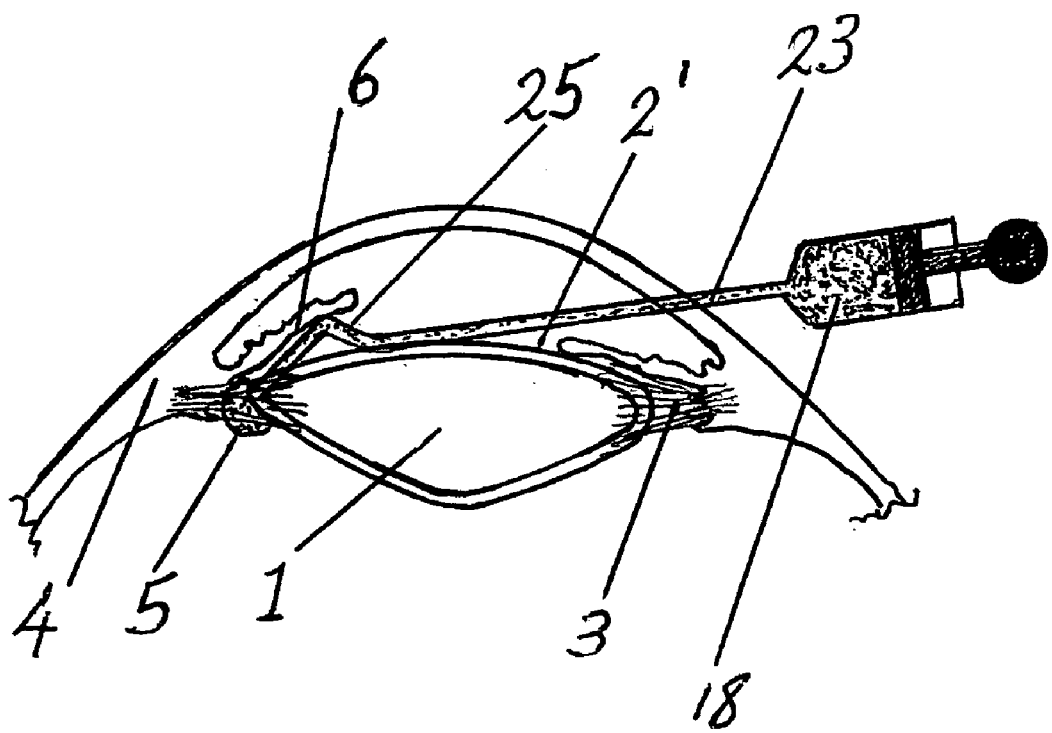
FIG. 14 depicts another configuration for another surgical procedure employing a specially designed cannula for the placement of the mini-bridges during the normal cataract surgery.

FIG. 14 depicts yet another configuration for an alternative surgical procedure employing a specially designed cannula 23 to enable the surgeon to place the accommodating zonular mini-bridge support system 5 for the eye lens 1 after cataract extraction. In this configuration, the surgeon can clearly see the ciliary muscle 4/zonules 3/Hannover canal 9, eye lens 1, lens capsule 2', while the surgeon places the mini-bridge implants 5 by a specially designed cannula 23. The method described is the use of mini-bridges 5 after cataract extraction, with the concurrent use of the foldable intraocular lens 1 for accommodative purposes. The technique involves performing cataract extraction using either clear cornea or scleral tunnel approach. Once the normal capsulorhexis and phacoemulsification of the nuclear and cortical material is performed, the anterior capsular bag 2' remains with its normal zonular attachments. The goal is to place the mini-bridges 5 at the position of the anterior capsule 2', in the usual case at 3 and 9 o'clock positions on the lens. The placement of the mini-bridges 5 can be performed either before the foldable intraocular lens 1 is placed in the capsule, or after the lens 1 is placed in the capsule and its haptics rotated to the 3 and 9 o'clock positions. The technique involves retracting the already dilated iris 6 (3 and 9 o'clock) positions, and placement of the mini-bridges 5, either in the form of composite liquid form or gel form, into the respected positions in the Hannover canal 9, thus bridging the ciliary muscle 4 to the anterior capsule 2'. This will involve a specific designed cannula 23. The shape of the preferred specific designed cannula is shown in FIG. 14. As shown the curved end 25 of the cannula 23 lifts the iris 6, while the liquid or gel is injected into the respective positions. The final placement of these mini-bridges can be determined either by an ultrasonic biomicroscope (UBM) or by direct endoscopic means. Although only four mini-bridges are shown, different arrangements of bridges can be used, such as three or more symmetrically spaced mini-bridges around the lens capsule. A single ring shaped mini-bridge can also be used (not shown).

Thus, the present invention, creates active pressure-transmitting zonule fiber-reinforced mini-bridges or force carrying webs between the interior surfaces of the ciliary body/muscle/processes and the exterior zonular surfaces of the eye lens capsule, circularly squeezing the eye lens capsule when the ciliary muscle contracts in close vision situations, in such a way to actively change the curvature of the eye lens, bringing its focal point to finally coincide with the retina/macula region and thus correct presbyopia and hyperopia on demand.

The surgical procedure proposed first uses a ciliary muscle relaxant to create a taut configuration for the lens/zonules/ciliary muscle assembly and then employs an ultrasonic biomicroscope (UBM) to enable the surgeon to clearly see, on a TV monitor, the ciliary muscle/zonules/Hannover canal, lens capsule, iris, mini-bridges, surgical tools, and thus be able to perform endoscopic or incisional surgery to place such mini-bridge implants in and around zonular cavities, such as, preferably the canal of Hannover so that the two ends of the mini-bridges span the internal surfaces of the ciliary muscle to the exterior surface of the natural eye capsule. In general other materials such as Nylon, Proline, light curable polymers or Heparin or other biologically active compounds to reduce body rejection of the mini-bridges can also be used.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, are hereby incorporated by reference.

What is claimed is:

1. A method of correcting presbyopia and hyperopia on demand, the method comprising the steps of:
    a. affixing at least one bridge in and around at least one set of natural zonular fibers of the eye;
    b. transmitting a contraction force from the ciliary muscles to the at least one set of natural zonular fibers;
    c. augmenting the contraction force by the at least one bridge affixed to the at least one set of natural zonular fibers; and
    d. constricting the natural crystalline lens by the augmented contraction force from the transmission of the contraction force from the ciliary muscles to the at least one set of natural zonular fibers and the at least one bridge.

* * * * *